(12) United States Patent
Fuentes-Ortega et al.

(10) Patent No.: US 11,540,878 B2
(45) Date of Patent: Jan. 3, 2023

(54) BLOOMING LEAFLET CATHETER WITH HIGH DENSITY ELECTRODE ARRAY

(71) Applicant: Biosense Webster (Israel) Ltd., Yokneam (IL)

(72) Inventors: Cesar Fuentes-Ortega, Pasadena, CA (US); Pieter E. Van Niekerk, Monrovia, CA (US); Shubhayu Basu, Anaheim, CA (US); John J. Foley, Rancho Palos Verdes, CA (US); Dustin R. Tobey, San Dimas, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 78 days.

(21) Appl. No.: 16/897,390

(22) Filed: Jun. 10, 2020

(65) Prior Publication Data

US 2021/0015551 A1    Jan. 21, 2021

Related U.S. Application Data

(60) Provisional application No. 62/875,152, filed on Jul. 17, 2019.

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/0016* (2013.01);
(Continued)

(58) Field of Classification Search
CPC .. A61B 2018/0016; A61B 2018/00267; A61B 2018/142; A61B 2018/1465;
(Continued)

(56) References Cited

U.S. PATENT DOCUMENTS

| 5,738,096 A | 4/1998 | Ben-Haim |
| 6,325,972 B1 | 12/2001 | Jacobs et al. |

(Continued)

FOREIGN PATENT DOCUMENTS

| DE | 10345023 A1 * | 4/2005 | ............ A61B 18/14 |
| DE | 102013103985 B3 | 10/2014 | |

(Continued)

OTHER PUBLICATIONS

U.S. Appl. No. 62/819,738, filed Mar. 18, 2019, by Basu et al., entitled: "Electrode Configurations for Diagnosis of Arrhythmias."

(Continued)

*Primary Examiner* — Jaymi E Della

(74) *Attorney, Agent, or Firm* — Frost Brown Todd LLC

(57) ABSTRACT

An apparatus includes a catheter shaft assembly and an end effector. The catheter shaft assembly includes an outer sheath with a distal end. The end effector is associated with a distal end of the catheter shaft assembly. The end effector includes a plurality of leaflets. The leaflets are configured to transition between a first configuration and a second configuration. The leaflets are configured to fit within the outer sheath in the first configuration. The leaflets are configured to expand outwardly away from the longitudinal axis in the second configuration in response to being exposed distally relative to the distal end of the outer sheath. Each leaflet includes a flexible body and a plurality of electrodes. Each flexible body defines a plurality of openings. The electrodes are positioned on the flexible body.

20 Claims, 9 Drawing Sheets

(52) U.S. Cl.
CPC ............... *A61B 2018/00267* (2013.01); *A61B 2018/00577* (2013.01); *A61B 2018/126* (2013.01); *A61B 2018/142* (2013.01); *A61B 2018/1405* (2013.01); *A61B 2018/1465* (2013.01); *A61B 2018/1467* (2013.01); *A61B 2018/1475* (2013.01)

(58) Field of Classification Search
CPC .... A61B 2018/1467; A61B 2018/1475; A61B 18/1492
See application file for complete search history.

(56) References Cited

U.S. PATENT DOCUMENTS

| | | | |
|---|---|---|---|
| 6,365,102 | B1 | 4/2002 | Wu et al. |
| 6,447,719 | B1 | 9/2002 | Agamohamadi et al. |
| 6,852,277 | B2 | 2/2005 | Platt, Jr. et al. |
| 6,852,279 | B2 | 2/2005 | Williams et al. |
| 6,939,519 | B2 | 9/2005 | Agamohamadi et al. |
| 7,468,062 | B2 | 12/2008 | Oral et al. |
| 8,636,732 | B2 | 1/2014 | Davis et al. |
| 8,956,353 | B2 | 2/2015 | Govari et al. |
| 9,314,299 | B2 | 4/2016 | Fang |
| 9,480,416 | B2 | 11/2016 | Govari et al. |
| 9,801,585 | B2 | 10/2017 | Shah et al. |
| 9,907,480 | B2 | 3/2018 | Basu et al. |
| 10,061,198 | B2 | 8/2018 | Lima De Miranda |
| 10,130,423 | B1 | 11/2018 | Viswanathan et al. |
| 10,130,442 | B2 | 11/2018 | Dor et al. |
| 10,561,753 | B2 | 2/2020 | Thompson et al. |
| 10,660,700 | B2 | 5/2020 | Beeckler et al. |
| 10,702,177 | B2 | 7/2020 | Aujla |
| 10,743,932 | B2 | 8/2020 | Gallardo et al. |
| 2008/0243116 | A1* | 10/2008 | Anderson .......... A61B 18/1492 606/41 |
| 2016/0338770 | A1* | 11/2016 | Bar-Tal .............. A61B 18/1492 |
| 2016/0346040 | A1 | 12/2016 | Hall et al. |
| 2017/0112405 | A1* | 4/2017 | Sterrett .................. A61B 5/287 |
| 2018/0071017 | A1 | 3/2018 | Bar-Tal et al. |
| 2018/0085160 | A1* | 3/2018 | Viswanathan ......... A61N 1/371 |

FOREIGN PATENT DOCUMENTS

| | | |
|---|---|---|
| DE | 102014101348 A1 | 8/2015 |
| DE | 10201-130152 B3 | 1/2019 |
| EP | 1529548 A2 | 5/2005 |
| EP | 3025196 | 6/2016 |
| WO | WO 2015/011253 A1 | 1/2015 |
| WO | WO 2015/117908 A1 | 8/2015 |
| WO | WO 2015/140741 A1 | 9/2015 |
| WO | WO-2015140741 A1 * | 9/2015 ......... A61B 18/1206 |

OTHER PUBLICATIONS

U.S. Appl. No. 62/875,152, filed Jul. 17, 2019 by Fuentes-Ortega et al., entitled "Blooming Leaflet Catheter With High Density Electrode Array."

International Search Report and Written Opinion dated Nov. 4, 2020, for International Application No. PCT/US2020/041354, 12 pages.

* cited by examiner

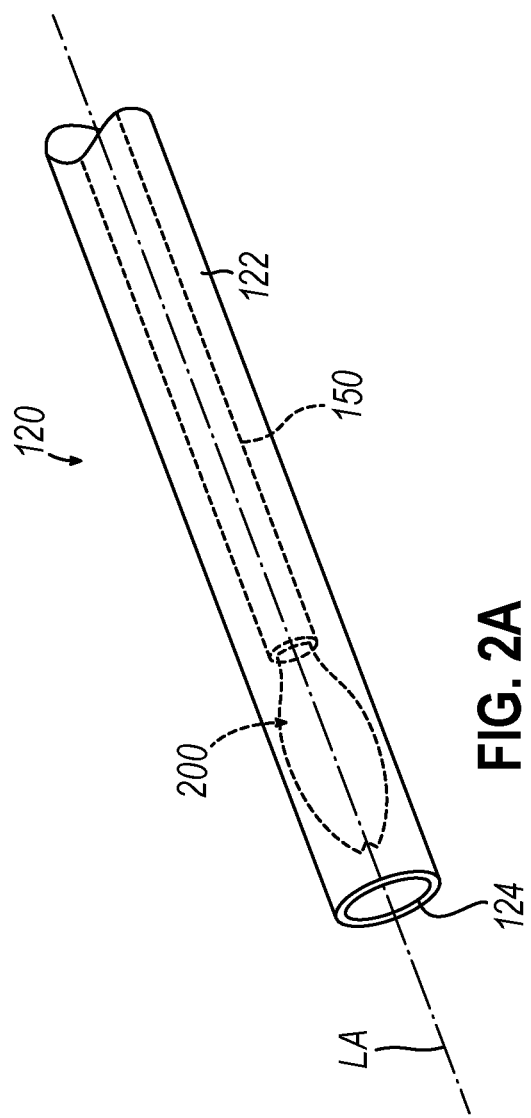

BLOOMING LEAFLET CATHETER WITH HIGH DENSITY ELECTRODE ARRAY

PRIORITY

This application claims priority to U.S. Provisional Pat. App. No. 62/875,152, entitled "Blooming Leaflet Catheter with High Density Electrode Array," filed Jul. 17, 2019, the disclosure of which is incorporated by reference herein in its entirety.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad or other reference electrode that is in contact with the patient.

Examples of ablation catheters are described in U.S. Pub. No. 2013/0030426, entitled "Integrated Ablation System using Catheter with Multiple Irrigation Lumens," published Jan. 31, 2013, issued as U.S. Pat. No. 10,743,932 on Aug. 18, 2020, the disclosure of which is incorporated by reference herein in its entirety; U.S. Pub. No. 2017/0312022, entitled "Irrigated Balloon Catheter with Flexible Circuit Electrode Assembly," published Nov. 2, 2017, issued as U.S. Pat. No. 10,660,700 on May 26, 2020, the disclosure of which is incorporated by reference herein in its entirety; U.S. Pub. No. 2018/0071017, entitled "Ablation Catheter with a Flexible Printed Circuit Board," published Mar. 15, 2018, the disclosure of which is incorporated by reference herein in its entirety; U.S. Pub. No. 2018/0056038, entitled "Catheter with Bipole Electrode Spacer and Related Methods," published Mar. 1, 2018, issued as U.S. Pat. No. 10,702,177 on Jul. 7, 2020, the disclosure of which is incorporated by reference herein in its entirety; U.S. Pat. No. 10,130,422, entitled "Catheter with Soft Distal Tip for Mapping and Ablating Tubular Region," issued Nov. 20, 2018, the disclosure of which is incorporated by reference herein in its entirety; U.S. Pat. No. 8,956,353, entitled "Electrode Irrigation Using Micro-Jets," issued Feb. 17, 2015, the disclosure of which is incorporated by reference herein in its entirety; and U.S. Pat. No. 9,801,585, entitled "Electrocardiogram Noise Reduction," issued Oct. 31, 2017, the disclosure of which is incorporated by reference herein in its entirety.

Some catheter ablation procedures may be performed after using electrophysiology (EP) mapping to identify tissue regions that should be targeted for ablation. Such EP mapping may include the use of sensing electrodes on a catheter (e.g., the same catheter that is used to perform the ablation or a dedicated mapping catheter). Such sensing electrodes may monitor electrical signals emanating from conductive endocardial tissues to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein in its entirety. Examples of EP mapping catheters are described in U.S. Pat. No. 9,907,480, entitled "Catheter Spine Assembly with Closely-Spaced Bipole Microelectrodes," issued Mar. 6, 2018, the disclosure of which is incorporated by reference herein in its entirety; U.S. Pat. No. 10,130,422, entitled "Catheter with Soft Distal Tip for Mapping and Ablating Tubular Region," issued Nov. 20, 2018, the disclosure of which is incorporated by reference herein in its entirety; and U.S. Pub. No. 2018/0056038, entitled "Catheter with Bipole Electrode Spacer and Related Methods," published Mar. 1, 2018, issued as U.S. Pat. No. 10,702,177 on Jul. 7, 2020, the disclosure of which is incorporated by reference herein in its entirety.

In addition to using EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, Calif. Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein in its entirety; and various other references that are cited herein.

While several catheter systems and methods have been made and used, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

FIG. 2A depicts a perspective view of a distal portion of the catheter of FIG. 1, with an end effector of the catheter in a proximal position relative to an outer sheath of the catheter;

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. Overview of Exemplary Catheter System

Figure 1:
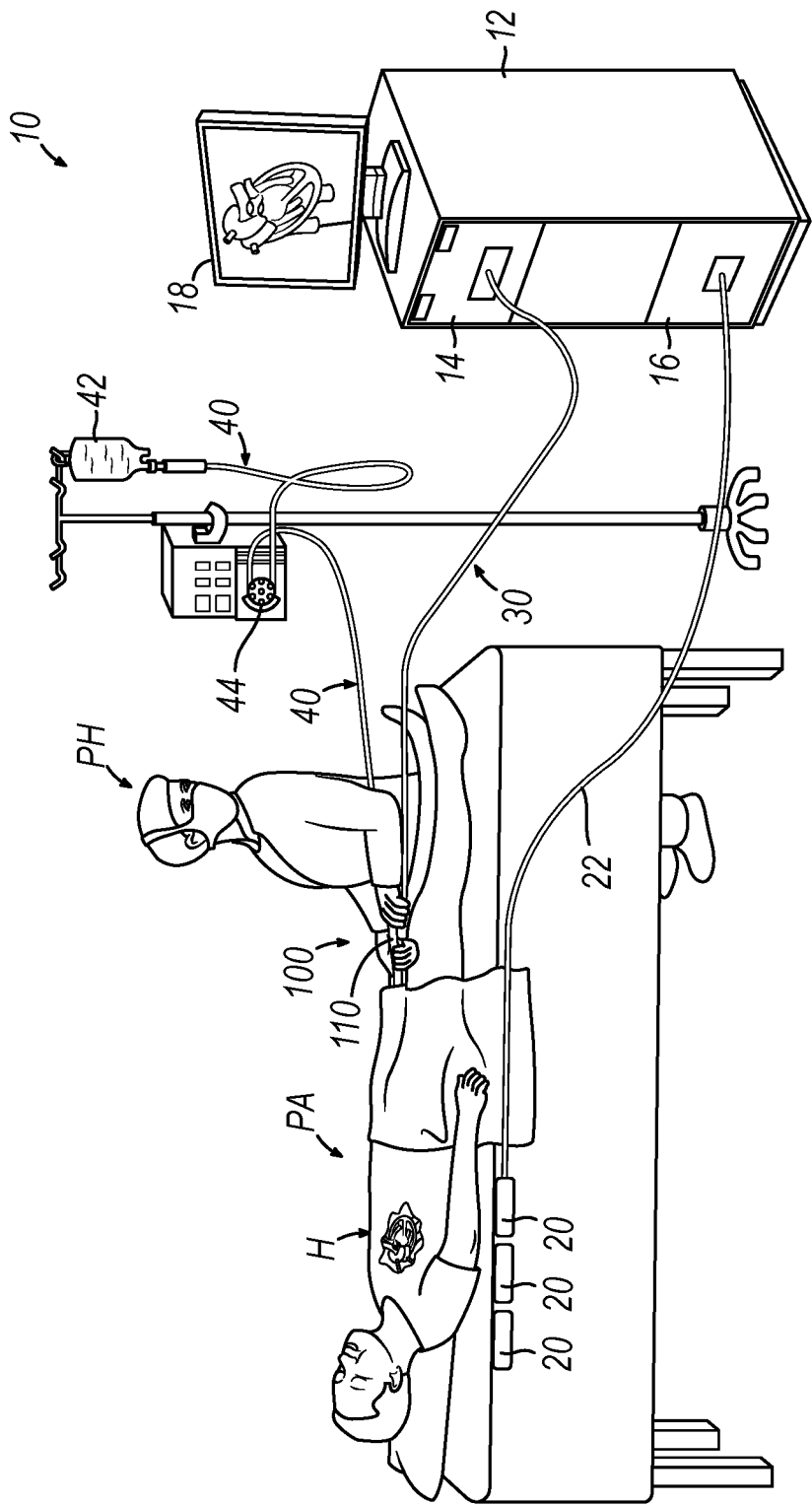
FIG. 1 depicts a schematic view of a medical procedure in which a catheter of a catheter assembly is inserted in a patient.

FIG. 1 shows an exemplary medical procedure and associated components of a cardiac ablation system. In particular, FIG. 1 shows a physician (PH) grasping a handle (110) of a catheter assembly (100), with an end effector (200) of a flexible catheter (120) (shown in FIGS. 2A-3 but not shown in FIG. 1) of catheter assembly (100) disposed in a patient (PA) to map or ablate tissue in or near the heart (H) of the patient (PA). As shown in FIGS. 2A-3, catheter (120) includes an outer sheath (122), with end effector (200) being disposed at or near a distal end (124) of outer sheath (122). Catheter assembly (100) is coupled with a guidance and drive system (10) via a cable (30). Catheter assembly (100) is also coupled with a fluid source (42) via a fluid conduit (40), though this is merely optional. A set of field generators (20) are positioned underneath the patient (PA) and are also coupled with guidance and drive system (10) via a cable (22).

Guidance and drive system (10) of the present example includes a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via electrodes (250) of end effector (200) as described in greater detail below. Console (12) includes a processor (not shown) that processes such EP mapping signals and thereby provides EP mapping as is known in the art. In addition, or in the alternative, first driver module (14) may be operable to provide RF power to electrodes (260) of end effector (200) to thereby ablate tissue. In some versions, first driver module (14) is also operable to receive position indicative signals from one or more position sensors (270) in end effector (200), as will be described in greater detail below. In such versions, the processor of console (12) is also operable to process the position indicative signals from the position sensors (270) to thereby determine the position of the end effector (200) of catheter (120) within the patient (PA).

Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

Display (18) is coupled with the processor of console (12) and is operable to render images of patient anatomy. Such images may be based on a set of preoperatively or intraoperatively obtained images (e.g., a CT or MM scan, 3-D map, etc.). The views of patient anatomy provided through display (18) may also change dynamically based on signals from the position sensor of end effector (200). For instance, as end effector (200) of catheter (120) moves within the patient (PA), the corresponding position data from the position sensor may cause the processor of console (12) to update the patient anatomy views in display (18) in real time to depict the regions of patient anatomy around end effector (200) as end effector (200) moves within the patient (PA). Moreover, the processor of console (12) may drive display (18) to show locations of aberrant conductive tissue sites, as detected via EP mapping with end effector (200). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (200) on the images of the patient's anatomy, such as by superimposing an illuminated dot, a crosshair, a graphical representation of end effector (200), or some other form of visual indication. Such a superimposed visual indication may also move within the images of the patient anatomy on display (18) in real time as the physician moves end effector (200) within the patient (PA), thereby providing real-time visual feedback to the operator about the position of end effector (200) within the patient (PA) as end effector (200) moves within the patient (PA). The images provided through display (18) may thus effectively provide a video tracking the position of end effector (200) within a patient (PA), without necessarily having any optical instrumentation (i.e., cameras) viewing end effector (200). In the same view, display (18) may simultaneously visually indicate the locations of aberrant conductive tissue sites detected through the EP mapping as described herein. The physician (PH) may thus view display (18) to observe the real time positioning of end effector (200) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). In some variations, conduit (40), fluid source (42), and pump (44) are omitted entirely. In versions where these components are included, end effector (200) may be configured to communicate irrigation fluid from fluid source (42) to the target site in the patient. Such irrigation may be provided in accordance with the teachings of any of the various patent references cited herein; or in any other suitable fashion as will be apparent to those skilled in the art in view of the teachings herein.

II. Exemplary End Effector

FIGS. 2A-3 show end effector (200) in greater detail. As shown, end effector (200) includes a set of leaflets (210) that are compressible to fit within an outer sheath (122). End effector (200) is mounted to an inner shaft (150), which is internal to outer sheath (122) and is slidably disposed relative to outer sheath (122). FIG. 2A shows a state in which end effector (200) is retracted proximally relative to outer sheath (122), such that end effector (200) is proximal to distal end (124) of outer sheath (122). In this state, end effector (200) deformably conforms to the cylindraceous interior of outer sheath (122). Catheter (120) and end effector (200) may be in the state shown in FIG. 2A when catheter (120) is introduced into the body of the patient (PA); and during transit from the insertion site to the targeted cardiovascular region within the patient (PA).

Figure 2B:
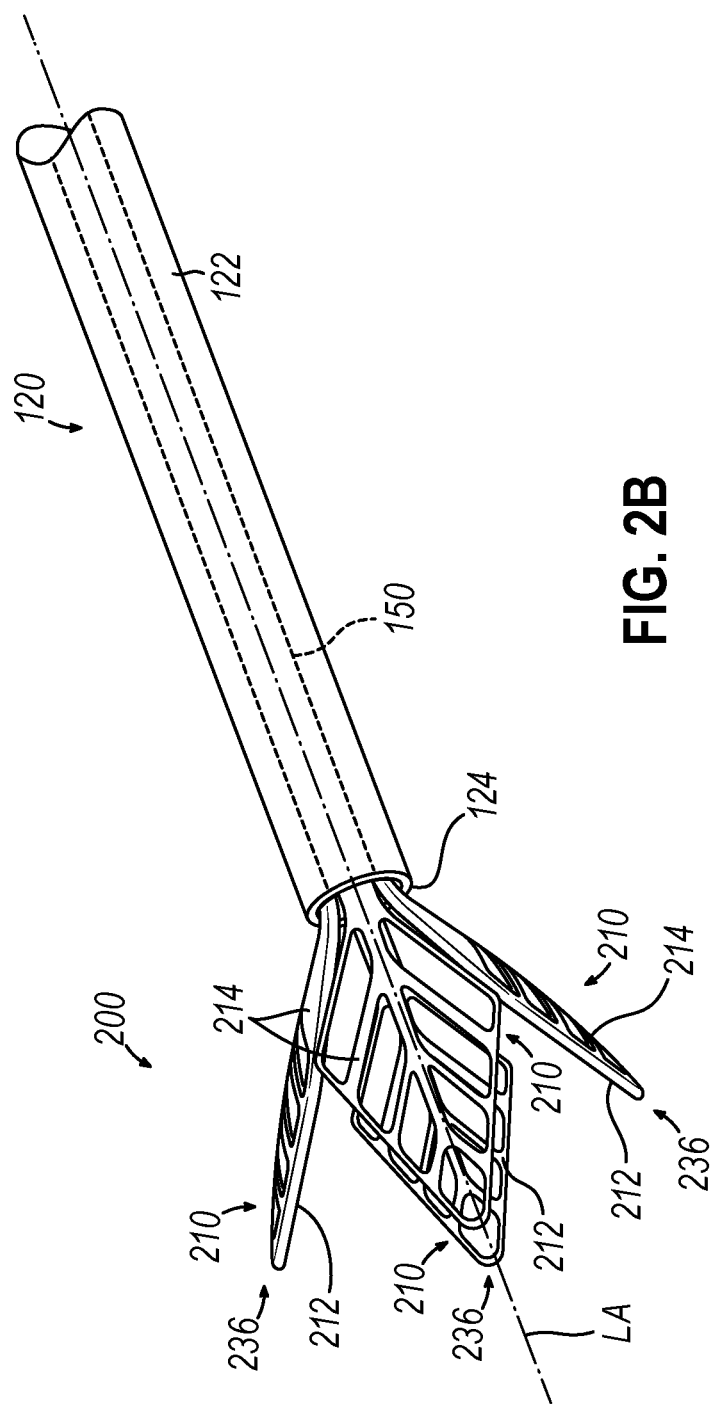
FIG. 2B depicts a perspective view of the distal portion of FIG. 2A, with the end effector in a distal position relative to the outer sheath, and with the end effector in an outwardly splayed state.
Figure 3:
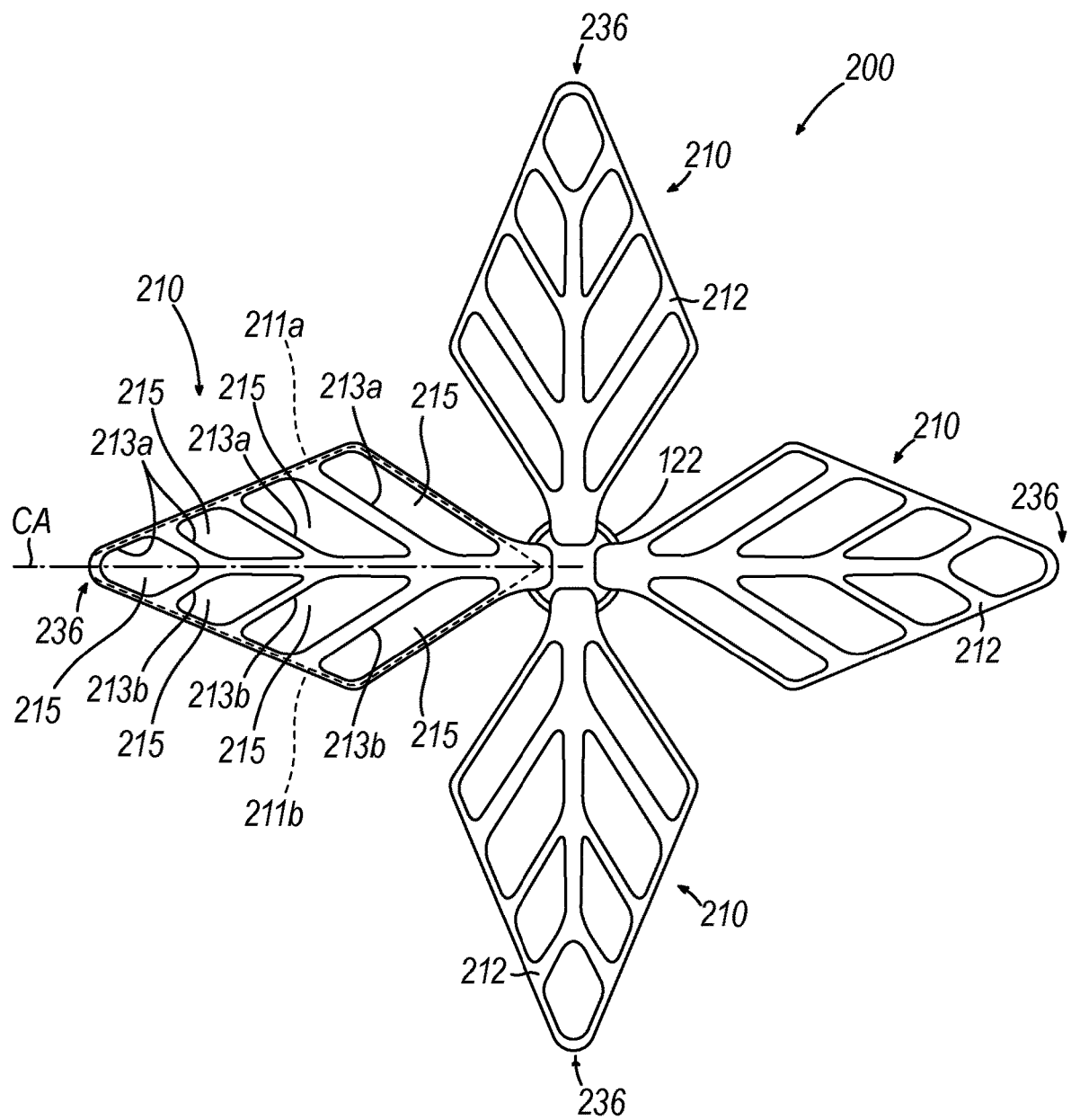
FIG. 3 depicts an end view of the end effector of FIG. 2A, viewed from the proximal end of the end effector, with the end effector in an expanded and flattened state.

FIG. 2B shows a state in which end effector (200) is advanced distally relative to outer sheath (122), such that end effector (200) is distal to distal end (124) of outer sheath (122). As shown in FIG. 2B, leaflets (210) are resiliently biased toward an outwardly splayed configuration, such that distal ends (236) of leaflets (210) diverge away from the longitudinal axis (LA) of catheter (120). End effector (200) thus presents a bloomed flower-like configuration in this state. In this state, inner surfaces (212) and outer surfaces (214) of leaflets (210) are exposed.

In some versions, in order to transition between the state shown in FIG. 2A and the state shown in FIG. 2B, inner shaft (150) remains longitudinally stationary relative to handle (110) while outer sheath (122) translates longitudinally relative to handle (110) and relative to inner shaft (150). In such versions, handle (110) or the proximal end of outer sheath (122) may include an actuator that may be manipulated by the physician (PH) to drive outer (122) sheath longitudinally relative to handle (110) and relative to inner shaft (150). As another merely illustrative variation, in order to transition between the state shown in FIG. 2A and the state shown in FIG. 2B, outer sheath (122) remains longitudinally stationary relative to handle (110) while inner shaft (150) translates longitudinally relative to handle (110) and relative to outer sheath (122). In such versions, handle (110) may include an actuator that may be manipulated by the physician (PH) to drive inner shaft (150) longitudinally relative to handle (110) and relative to outer sheath (122).

Figure 2C:
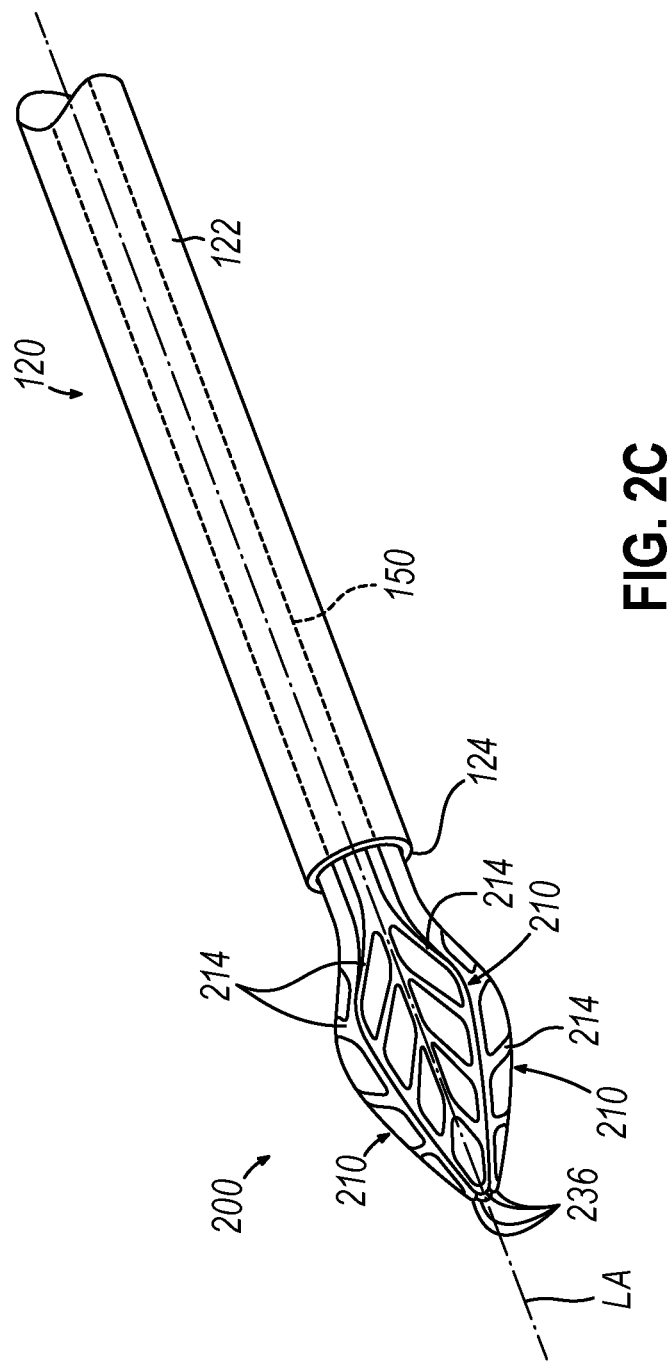
FIG. 2C depicts a perspective view of the distal portion of FIG. 2A, with the end effector in the distal position relative to the outer sheath, and with the end effector in a bulbous state.

FIG. 2C shows a state in which end effector (200) is in the distal position relative to outer sheath (122), but with leaflets (210) in a bulbous configuration. In this state, distal ends (236) are convergingly oriented toward the longitudinal axis (LA) of catheter (120), while the intermediate regions of leaflets (210) bow outwardly away from the longitudinal axis (LA) of catheter (120). End effector (200) thus presents a generally bulbous configuration in this state. In this state, inner surfaces (212) of leaflets (210) are obscured while and outer surfaces (214) of leaflets (210) are exposed. Merely illustrative examples of ways in which end effector may transition between the state shown in FIG. 2B and the state shown in FIG. 2C will be described in greater detail below; while other ways will be apparent to those skilled in the art in view of the teachings herein.

FIG. 3 shows a state in which end effector (200) is in an expanded and flattened state. In this state, leaflets (210) are substantially co-planar with each other, with distal ends (236) of leaflets (210) diverging away from the longitudinal axis (LA) of catheter (120). End effector (200) may achieve this state when the physician (PH) starts with end effector (200) being in the state shown in FIG. 2B; then presses end effector (200) distally against an anatomical structure (e.g., cardiac wall, pulmonary vein, etc.) such that end effector (200) flattens out. In such a scenario, inner surfaces (212) of leaflets (210) may press directly against the tissue of the anatomical structure. By contrast, if the physician presses end effector (200) against an anatomical structure when end effector is in the state shown in FIG. 2C, outer surfaces (214) will press directly against the tissue of the anatomical structure.

As best seen in FIG. 3, end effector (200) of the present example includes four leaflets (210), which are angularly spaced apart from each other equidistantly about the longitudinal axis (LA) of catheter (120). Alternatively, any other suitable number of leaflets (210) may be used, including but not limited to two leaflets (210), three leaflets (210), or more than four leaflets (210). As used herein, the term "leaflet" denotes a shape that mimics an overall plant-like structure typically bounded by an outer line (211a) with another outer line (211b) (which may be a mirror image of the first outer line (211a) whereby both lines (211a, 211b) are referenced to a centerline (CA) with multiple connectors (213a, 213b) extending from the centerline (CA) to different locations on each of the boundary lines (211a, 211b). The connectors (213a, 213b) may have the same lengths or different lengths (e.g., as shown in FIG. 3). A membrane (215) may be provided between the adjacent connectors (213a, 213b) or alternatively, empty space (215') not shown) can be utilized in place of membrane (215). It is also noted that connectors (213a, 213b) are not necessary in some of the leaflet examples described herein (e.g., the examples shown in FIGS. 5-8).

As noted above, catheter assembly (100) of the present example is coupled with a fluid source (42) via a fluid conduit (40). A fluid conduit (not shown) extends along the length of catheter (120) and is operable to deliver irrigation fluid (e.g., saline) out through distal end (124) of catheter. For instance, the fluid conduit may distally terminate at distal end (124). Alternatively, end effector (200) may incorporate one or more irrigation ports that are in communication with the fluid conduit. In either case, the irrigation fluid may provide cooling, flushing, or other effects at end effector (200) during operation of end effector (200) within the patient (PH). Various suitable ways in which catheter assembly (100) may provide irrigation will be apparent to those skilled in the art. Alternatively, some variations of catheter assembly (100) may lack irrigation capabilities, such that conduit (40), fluid source (42), and pump (44) may be omitted.

In addition to the foregoing, end effector (200) and other aspects of catheter assembly (100) may be configured and operable in accordance with at least some of the teachings of U.S. Pub. No. 2018/0056038, issued as U.S. Pat. No. 10,702, 177 on Jul. 7, 2020, the disclosure of which is incorporated by reference herein in its entirety.

III. Exemplary End Effector Leaflet

Figure 4:
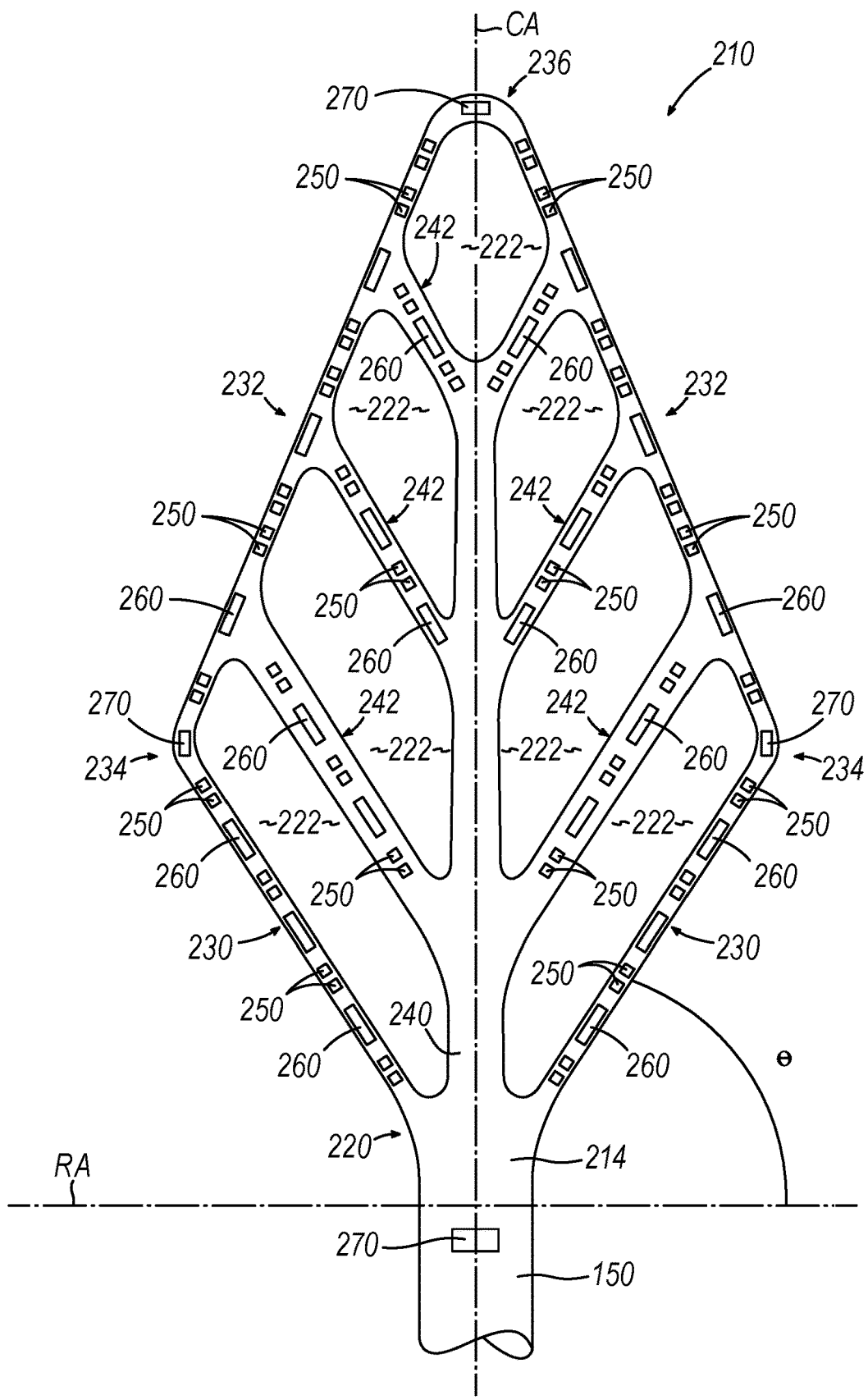
FIG. 4 depicts an enlarged plan view of a leaflet of the end effector of FIG. 2A.

FIG. 4 depicts a single leaflet (210) of end effector (200) in greater detail. Leaflet (210) of this example includes a body (220) with a plurality of electrodes (250, 260) and sensors (270) secured thereto. Body (220) of the present example is flexible and has a generally flat, planar configuration. By way of example only, body (220) may be formed of polyimide, polyether ether ketone, or any other suitable flex circuit substrate. A proximal end of body (220) is fixedly secured to inner shaft (150). In the present example, bodies (214) of all leaflets (210) of end effector (200) are secured to the same inner shaft (150). In some other versions, each leaflet (210) is secured to its own inner shaft (150). In versions where each leaflet (210) is secured to its own inner shaft (150), the inner shafts (150) may be secured to each other (e.g., in a bundle) or may independently movable relative to each other.

Body (220) of the present example includes a central spine member (240), a pair of proximal outer members (230) that diverge outwardly from central spine member (240) and from the proximal end of body (220), and a pair of distal outer members (232) that converge inwardly toward distal end (236) of leaflet (210). By way of example only, each proximal outer member (230) may define an angle (Θ) with a reference axis (RA), which is perpendicular to the central axis (CA) of leaflet (210), from approximately 45° to approximately 60°. Alternatively, any other suitable angle (Θ) may be provided. Each proximal outer member (230) transitions to a corresponding distal outer member (232) at a rounded corner (234). The two distal outer members (232) meet each other at distal end (236), which is also in the form of a rounded corner. A set of inner members (242) extend outwardly from central spine member (240) to distal outer members (232), providing a formation similar to veins of a leaf Inner members (242), outer members (230, 232), and central spine member (240) cooperate to define openings (222) through body (220). Openings (222) may facilitate the flow of blood through leaflets (210) during use of end effector (200).

Leaflet (210) of the present example further includes several mapping electrodes (250), which are provided in pairs to provide bipolar sensing of potentials. More particularly, each pair of mapping electrodes (250) is configured to provide bipolar sensing of electrocardiogram signals as the pair of electrodes (250) is placed in contact with cardiovascular tissue. Thus, a pair of electrodes (250) may be considered as collectively forming a single "sensor." Each mapping electrode (250) may be coupled with a corresponding trace or other electrical conduit on body (220), thereby enabling signals picked up by mapping electrodes (250) to be communicated back through electrical conduits (not shown) in catheter (120) to console (12), which may process the signals to provide EP mapping to thereby identify locations of aberrant electrical activity within the cardiac anatomy. This may in turn allow the physician (PH) to identify the most appropriate regions of cardiac tissue to ablate (e.g., with RF energy, cryoablation, etc.), to thereby prevent or at least reduce the communication of aberrant electrical activity across the cardiac tissue.

As noted above, body (220) is flexible, such that body (220) may conform to the contours and other surface geometry of cardiac tissue when end effector (200) is pressed against cardiac tissue. The deformation of body (220) may promote full contact between two or more pairs of mapping electrodes (250) and cardiac tissue. Such contact may be further promoted by providing a substantial number of mapping electrodes (250) on body (220), as shown in FIG. 4. In particular, mapping electrodes (250) are provided along proximal outer members (230), along distal outer members (232), along inner members (242) in the present example. Having a substantial number of mapping electrodes (250) may enable end effector (200) to provide high density EP mapping through all four chambers of the heart (H), as several pairs of mapping electrodes (250) can provide electrocardiogram signal sensing at multiple regions of cardiac tissue simultaneously.

In some versions, mapping electrodes (250) are also provided along central spine member (240). As also shown in FIG. 4, mapping electrodes (250) are positioned on outer surfaces (214) of leaflets (210) in this example. In addition, or in the alternative, mapping electrodes (250) may be positioned on inner surfaces (212) of leaflets (210). It should also be understood that the positioning of mapping electrodes (250) in the particular locations shown in FIG. 4 is merely illustrative. Mapping electrodes (250) may be provided in any other suitable number and arrangement along leaflet (210) as will be apparent to those skilled in the art in view of the teachings herein. As another merely illustrative example, one or more ring electrodes (not shown) may be positioned on outer sheath (122), near distal end (124), to provide a reference signal during EP mapping to enable factoring out of far field signals. Similarly, one or more one or more ring electrodes (not shown) may be positioned on inner shaft (150) for providing a reference signal. As yet another merely illustrative variation, mapping electrodes (250) may be omitted from end effector (200). In some such variations, ablation electrodes (260) are still included on end effector (200).

Leaflet (210) of the present example further includes several ablation electrodes (260). Ablation electrodes (260) are slightly larger than mapping electrodes (250) in this example. Ablation electrodes (260) may be used to apply RF energy to tissue that is in contact with electrodes (260), to thereby ablate the tissue. Each ablation electrode (260) may be coupled with a corresponding trace or other electrical conduit on body (220), thereby enabling console (12) to communicate RF energy through electrical conduits (not shown) in catheter (120) to the traces or other conduits on body (220) to reach ablation electrodes (260). While a substantial number of ablation electrodes (260) are shown in FIG. 4, it should be understood that in some scenarios, only one, only two, or some other relatively small number of ablation electrodes (260) would be activated to apply RF energy to tissue at any given moment. As with mapping electrodes (250), the number and positioning of ablation electrodes (260) as shown in FIG. 4 is merely illustrative. Any other suitable number or positioning may be used for ablation electrodes (260). While ablation electrodes (260) are shown on outer surface (214) in FIG. 4, ablation electrodes (160) may be positioned on inner surface (214) in addition to or in lieu of being positioned on outer surface (214). As another variation, in versions where body (220) is metallic (e.g., nitinol, etc.), at least a portion of body (220) may serve as an ablation electrode. For instance, one or more regions of body (220) may be exposed by insulative material, with such exposed regions serving as ablation electrodes. As yet another merely illustrative variation, ablation electrodes (260) may be omitted from end effector (200). In some such variations, mapping electrodes (250) are still included on end effector (200).

By way of example only, electrodes (250, 260) may be formed of platinum, gold, or any other suitable material. Electrodes (250, 260) may include various coatings, if desired. For instance, mapping electrodes (250) may include a coating that is selected to improve the signal-to-noise ratio of signals from mapping electrodes (250). Such coatings may include, but need not be limited to, iridium oxide (IrOx) coating, poly(3,4-ethylenedioxythiophene) (PEDOT) coating, Electrodeposited Iridium Oxide (EIROF) coating, Platinum Iridium (PtIr) coating, or any other suitable coating. Ablation electrodes (260) may include a coating that is selected to prevent adherence of blood to ablation electrodes (260). Various suitable kinds of coatings that may be used for electrodes (250, 260) will be apparent to those skilled in the art in view of the teachings herein.

By way of further example only, electrodes (250, 260) may spaced and arranged in accordance with at least some of the teachings of U.S. Provisional Patent App. No. 62/819, 738, entitled "Electrode Configurations for Diagnosis of Arrhythmias," filed Mar. 18, 2019, the disclosure of which is incorporated by reference herein in its entirety. For instance, electrodes (250, 260) may spaced and arranged in accordance with FIGS. 13A, 13B, 13C, and 13D of U.S. Provisional Patent App. No. 62/819,738.

Leaflet (210) of the present example further includes a plurality of position sensors (270). Each position sensor (270) is operable to generate signals that are indicative of the position and orientation of end effector (200) within the patient (PA). By way of example only, each position sensor (270) may be in the form of a wire coil or a plurality of wire coils (e.g., three orthogonal coils) that are configured to generate electrical signals in response to the presence of an alternating electromagnetic field generated by field generators (20). Each position sensor (270) may be coupled with a corresponding trace or other electrical conduit on body (220), thereby enabling signals generated by position sensors (270) to be communicated back through electrical conduits (not shown) in catheter (120) to console (12), which may process the signals to identify the position of leaflet (210) within the patient (PA). Other components and techniques that may be used to generate real-time position data associated with end effector (200) may include wireless triangulation, acoustic tracking, optical tracking, inertial tracking, and the like.

As shown in FIG. 4, a position sensor (270) is shown at distal end (236) of leaflet (210) and at each lateral rounded corner (234) of leaflet (210). Such positioning may enable console (12) to determine the three-dimensional position of leaflet (210) and the particular configuration of leaflet (210) (e.g., whether leaflet (210) is in one of the configurations shown in FIG. 2B, FIG. 2C, or FIG. 3). The number and positioning of position sensors (270) is merely optional. For instance, some variations may just provide a single position sensor (270) at distal end (236), without any additional position sensors (270) being provided on leaflet (210). In addition to including one or more position sensors (270) on leaflet (210), a position sensor (270) may be incorporated into the distal end of inner shaft (150) or outer sheath (122), etc. Some variations of leaflet (210) may lack a position sensor (270) altogether, regardless of whether a position sensor (270) is incorporated into the distal end of inner shaft (150) or outer sheath (122).

In the present example electrodes (250, 260), and in some cases even position sensors (270), may be provided on body (220) as a thin film through a physical vapor deposition (PVD) process. By way of example only, such a PVD process may be carried out in accordance with at least some of the teachings of International Patent Pub. No. WO 2015/117908, entitled "Medical Device for Ablating Tissue Cells and System Comprising a Device of This Type," published Aug. 13, 2015, the disclosure of which is incorporated by reference herein in its entirety; at least some of the teachings of German Patent Pub. No. 102017130152, entitled "Method for Operating a Multi-Layer Structure," published Jan. 3, 2019, the disclosure of which is incorporated by reference herein in its entirety; or at least some of the teachings of U.S. Pat. No. 10,061,198, entitled "Method for Producing a Medical Device or a Device with Structure Elements, Method for Modifying the Surface of a Medical Device or of a Device with Structure Elements, Medical Device and Laminated Composite with a Substrate," published Aug. 28, 2018, the disclosure of which is incorporated by reference herein in its entirety. Other methods may also be employed to provide electrodes (250, 260), position sensors (270), conductive traces, or other circuit components on body (220), including but not limited to sputter deposition, chemical vapor deposition (CVD), thermal deposition, etc. Regardless of the methods used, each leaflet (210) may ultimately constitute a flex circuit.

As noted above, each leaflet (210) is flexible enough to compress within outer sheath as shown in FIG. 2A; yet is resiliently biased toward the expanded configuration shown in FIG. 2B. In some variations, this resilience is provided by the material forming body (220). In some other variations, one or more resilient features (not shown) are added to body (220) to impart the resilient bias. By way of example only, one or more nitinol strips or other nitinol structures may be applied to body (220), such as along any one or more of inner members (242), outer members (230, 232), or central spine member (240). Such nitinol strips may be applied using the vapor deposition process or other manufacturing techniques noted above. In versions where electrodes (250, 260) are provided on inner surfaces (212) and on outer surfaces (214), the nitinol strips or other resilient members may be interposed between layers of the flexible material (e.g., polyimide, polyether ether ketone, etc.) forming body (220). Alternatively, the nitinol strips or other resilient members may be positioned along regions of body (220) where electrodes (250, 260) are not present.

In addition to providing a resilient bias toward the expanded configuration shown in FIG. 2B, resilient members such as nitinol structures may also bias each leaflet (210) toward having a flat configuration, a curved configuration, or any other suitable configuration. As yet another merely illustrative example, in versions where nitinol is incorporated into leaflet (210), the nitinol may be shape set to expand at human body temperature. As still another merely illustrative example, body (220) may be formed entirely of nitinol, with electrodes (250, 260) and position sensors (270) being applied directly onto an insulative layer provided over the nitinol of body (220). In such versions, body (220) may lack polyimide, polyether ether ketone, or other flexible materials that serve as conventional flex circuit substrates.

By way of example only, leaflet (210) may be approximately 20 mm long. By way of further example only, leaflet may have a width ranging from approximately 11 mm to approximately 15 mm. Alternatively, leaflet (210) may have any other suitable dimensions.

Figure 5:
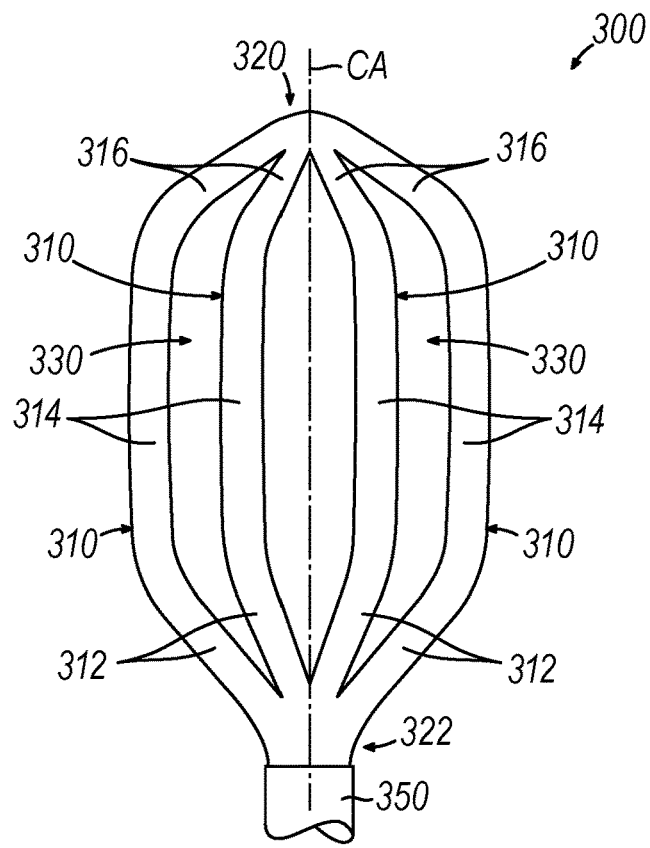
FIG. 5 depicts an enlarged plan view of an exemplary alternative leaflet.

FIG. 5 depicts another exemplary leaflet (300) that may be incorporated into end effector (200) in place of leaflet (210). Any suitable number and arrangement of leaflets (300) may be used to form the end effector. Leaflet (300) of this example includes a body (322) that is flexible and substantially flat or planar. Leaflet (300) is secured to a shaft (350), which may be slidably disposed relative to outer sheath (122) like shaft (150) described above. Body (322) of this example includes a set of strips (310) that converge at shaft (350) and at a distal end (320) of body (322), with gaps (330) being defined between strips (310). Each strip (310) includes an outwardly diverging proximal member (312), which is oriented obliquely away from a central axis (CA) of body (322). Each strip (310) further includes a straight central member (314), extending distally from the corresponding proximal member (312) and parallel with the central axis (CA) of body (322). Each strip (312) further includes an inwardly converging distal member (316), extending distally from the corresponding straight central member (314) toward the central axis (CA) of body (322) to converge at distal end (320).

While not shown in FIG. 5, leaflet (300) may include any suitable number and arrangement of mapping electrodes like mapping electrodes (250) of leaflet (210). In addition, or in the alternative, leaflet (300) may include any suitable number and arrangement of ablation electrodes like ablation electrodes (260) of leaflet (210). In addition, or in the alternative, leaflet (300) may include any suitable number and arrangement of position sensors like position sensors (270) of leaflet (210). Leaflet (300) may also include integral nitinol strips or other resilient features to impart resilience to leaflet (300), thereby urging leaflet (300) to assume a particular shape or orientation when leaflet (300) is freed from the confines of outer sheath (122). As with body (220) of leaflet (210), body (322) of leaflet (300) may be formed of a conventional flex circuit substrate material (e.g., polyimide, polyether ether ketone, etc.); and the electrodes and other metallic features of leaflet (300) may be vapor deposited onto body (322). Other suitable ways in which leaflet (300) may be formed will be apparent to those skilled in the art in view of the teachings herein.

Figure 6:
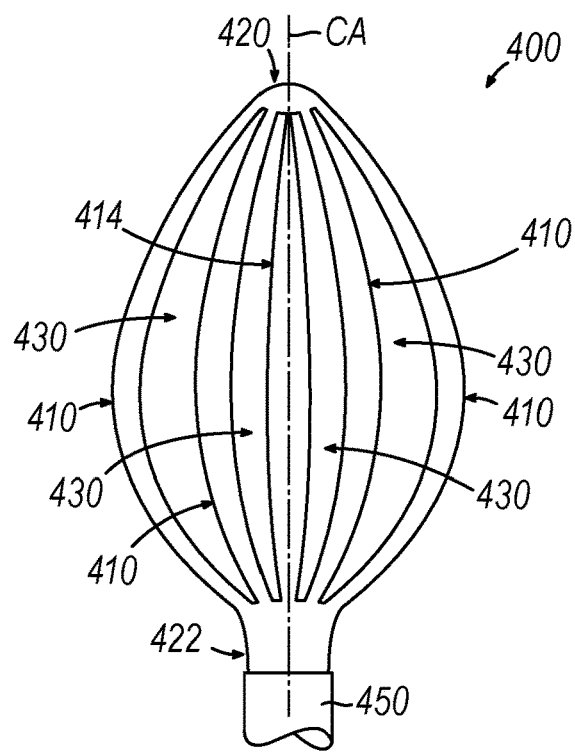
FIG. 6 depicts an enlarged plan view of another exemplary alternative leaflet.

FIG. 6 depicts another exemplary leaflet (400) that may be incorporated into end effector (200) in place of leaflet (210). Any suitable number and arrangement of leaflets (400) may be used to form the end effector. Leaflet (400) of this example includes a body (22) that is flexible and substantially flat or planar. Leaflet (400) is secured to a shaft (450), which may be slidably disposed relative to outer sheath (122) like shaft (150) described above. Body (422) of this example includes a set of strips (410, 414) that converge at shaft (450) and at a distal end (420) of body (422), with gaps (430) being defined between strips (410). Each outer strip (410) bows outwardly away from a central axis (CA) of body (422). Central strip (414) extends along a straight path that is aligned with the central axis (CA) of body (422).

While not shown in FIG. 6, leaflet (400) may include any suitable number and arrangement of mapping electrodes like mapping electrodes (250) of leaflet (210). In addition, or in the alternative, leaflet (400) may include any suitable number and arrangement of ablation electrodes like ablation electrodes (260) of leaflet (210). In addition, or in the alternative, leaflet (400) may include any suitable number and arrangement of position sensors like position sensors (270) of leaflet (210). Leaflet (400) may also include integral nitinol strips or other resilient features to impart resilience to leaflet (400), thereby urging leaflet (400) to assume a particular shape or orientation when leaflet (400) is freed from the confines of outer sheath (122). As with body (220) of leaflet (210), body (422) of leaflet (400) may be formed of a conventional flex circuit substrate material (e.g., polyimide, polyether ether ketone, etc.); and the electrodes and other metallic features of leaflet (400) may be vapor deposited onto body (422). Other suitable ways in which leaflet (400) may be formed will be apparent to those skilled in the art in view of the teachings herein.

While FIGS. 2B-6 depict several examples of configurations that the leaflets (210, 300, 400) may take, still other suitable configurations will be apparent to those skilled in the art in view of the teachings herein. By way of example only, leaflets (210, 300, 400) may be diamond-shaped, shaped like a palm leaf, shaped like a ginko tree leaf, shaped like an aspen tree leaf, or otherwise shaped.

IV. Exemplary End Effector Expansion and Contraction Configurations

As noted above with reference to the transition from the state shown in FIG. 2B to the state shown in FIG. 2C, it may be desirable in some scenarios to transition an end effector like end effector (200) between a state where leaflets (210, 300, 400) are in an outwardly splayed configuration (e.g., like a bloomed flower) and a bulbous configuration (e.g., like a flower bud). By way of example only, it may be desirable to operate end effector (220) in an outwardly splayed configuration when end effector (200) is being used to perform EP mapping; and in a bulbous configuration when end effector (200) is being used to perform tissue ablation.

Alternatively, the selection between the outwardly splayed configuration and the bulbous configuration may vary based on the particular anatomical structure that the physician (PH) wishes to engage with end effector (200). The preferred configuration of end effector (200) may vary based on the geometry of the targeted anatomical structure, to ensure intimate contact with the tissue and as many electrodes (250) of end effector (200) as possible. For instance, a physician (PH) may prefer the bulbous configuration of FIG. 2C when operating within the pulmonary vein; and the splayed configuration of FIG. 2B when operating in chambers of the heart (H) (e.g., pressing end effector (200) against the wall of an atrium).

Other factors that may influence when a physician (PH) may wish to operate end effector (200) in an outwardly splayed configuration versus a bulbous configuration will be apparent to those skilled in the art in view of the teachings herein. Regardless of the purpose, it may be desirable to incorporate control features into catheter assembly (100) to enable the physician (PH) to selectively control whether end effector (200) is in an outwardly splayed configuration or a bulbous configuration. Merely illustrative examples of such control features are described in greater detail below; while other examples will be apparent to those skilled in the art in view of the teachings herein.

Figure 7B:
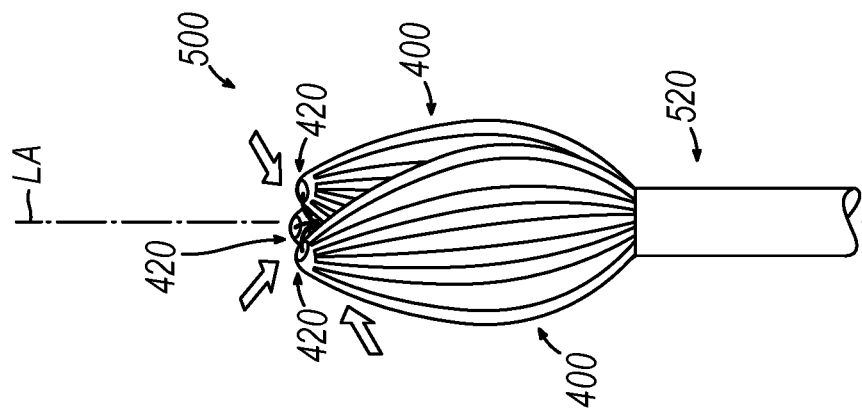
FIG. 7B depicts a side elevation view of the end effector of FIG. 7A, with the end effector in a bulbous state.
Figure 7A:
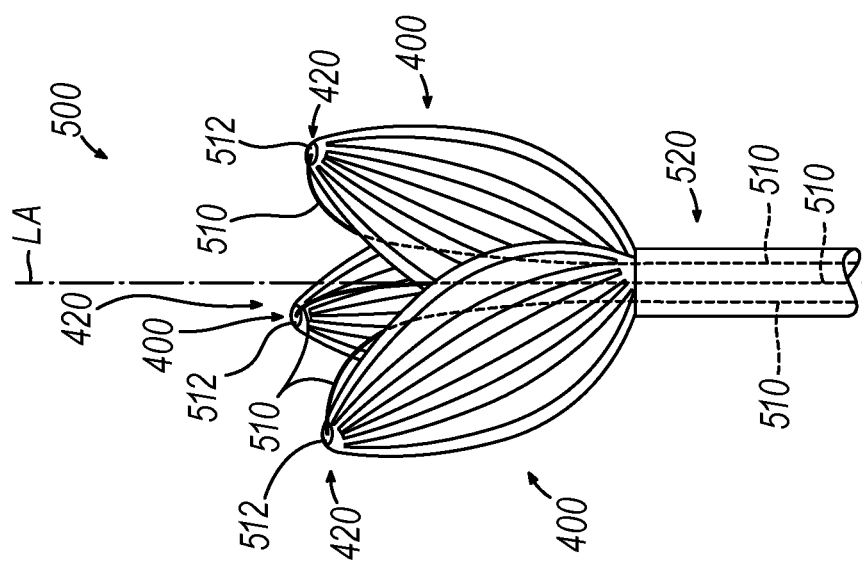
FIG. 7A depicts a side elevation view of an exemplary end effector incorporating the leaflet of FIG. 6, with the end effector in an outwardly splayed state.

FIGS. 7A-7B show an exemplary end effector (500) that includes leaflets (400) as described above. While leaflets (400) are incorporated into end effector (500) in this example, it should be understood that the below teachings may be readily applied to other versions of end effector (500) that incorporate other kinds of leaflets, including but not limited to leaflet (210) or leaflet (300). End effector (500) is at the distal end of an outer sheath (520), which may be substantially similar to sheath (122) described above. At the stage shown in FIG. 7A, end effector (500) has been freed from the confines of outer sheath (520), similar to end effector (200) being freed from the confines of outer sheath (122) as shown in FIG. 2A. At this stage, leaflets (400) of end effector (500) are in an outwardly splayed configuration.

In the example shown in FIG. 7A, control wires (510) are secured to connection points (512) at the inner sides of distal ends (420) of leaflets (400), such that each leaflet (400) has an associated control wire (510). Control wires (510) are fed through the interior of end effector (500), such that control wires (510) are interposed between leaflets (500) and the longitudinal axis (LA) of sheath (520). The proximal ends of control wires (510) may be coupled with a slider, a rotary knob, or any other suitable user input device at handle (110) of catheter assembly (100). When the physician (PH) wishes to transition from the outwardly splayed configuration of FIG. 7A to the bulbous configuration of FIG. 7B, the physician (PH) retracts control wires (510) proximally (e.g., by manipulating the corresponding user input device at handle (110) of catheter assembly (100)).

As control wires (510) retract proximally, distal ends (420) of leaflets (400) move toward the longitudinal axis (LA) of sheath (520), while the proximal ends of leaflets (400) remain stationary. Distal ends (420) eventually reach the position shown in FIG. 7B, thereby providing end effector (500) with a bulbous configuration. In this example, the resilience of leaflets (400) causes end effector (500) to have the bulbous configuration when distal ends (420) are drawn toward each other as shown in FIG. 7B. In other words, leaflets (400) may buckle in response to increased tension in control wires (510), thereby bowing outwardly to collectively define the bulbous shape shown in FIG. 7B. In some versions, leaflets (400) are pre-curved such that each leaflet (400) is resiliently biased to form a three-dimensionally curved profile. In particular, each leaflet (400) may be pre-curved with a concave curvature facing toward the longitudinal axis (LA) of sheath (520) and a convex curvature facing away from the longitudinal axis (LA) of sheath (520). Such a pre-curved configuration may further promote end effector (500) defining a bulbous or spheroid shape in response to increased tension in control wires (510) as shown in FIG. 7B.

In some instances, the physician (PH) may continue retracting control wires (510) proximally after reaching the state shown in FIG. 7B. In some such cases, distal ends (420) of leaflets (400) may begin to retract proximally, which may cause the longitudinally intermediate regions of leaflets (400) to bow further outwardly, thereby effectively widening end effector (500) while simultaneously reducing the overall length of end effector (500). Regardless of whether the physician (PH) provides this additional widening of end effector (500), end effector (500) may be pressed against tissue (e.g., cardiac tissue) when end effector (500) has a bulbous shape. When end effector (500) is pressed against tissue, the leaflet (400) or leaflets (400) that is or are in contact with the tissue may deform and thereby conform to the contours of the adjacent tissue. Such deformation and conformance may promote contact between several electrodes (250, 260) of the leaflet (400) or leaflets (400) and the adjacent tissues. In some instances, such contact will effectively include a grid of electrodes (250, 260) in contact with the tissue. In the case of electrodes (250), the contact with tissue allows EP mapping of the tissue. In the case of electrodes (260), the contact with tissue allows ablation of the tissue.

When the physician (PH) wishes to return end effector (500) back to the state shown in FIG. 7A from the state shown in FIG. 7B, the physician (PH) may simply release control wires (510). With tension being relieved in control wires (510), the resilience of leaves (400) may urge end effector (500) back to the state shown in FIG. 7A. After reaching this stage, the physician may return end effector (500) to the interior of outer sheath (520) (e.g., by retracting end effector (500) proximally relative to outer sheath (520) or by advancing outer sheath (520) distally relative end effector (500)); then withdraw the catheter from the patient (PA).

In some other variations of use of end effector (500), the physician (PH) retracts control wires (510) only to the point where leaflets (400) collectively form a basket shape or a tulip shape; and not to the point where leaflets (400) collectively form a bulbous shape or ball shape. To facilitate selective retraction of control wires (510), handle (110) of catheter assembly (100) may include one or more visual indicators, tactile detent features, or other user feedback features that may be associated with the user input device that drives translation of control wires (510). Such user feedback features may enable the physician (PH) to more easily control and determine the extent to which distal ends (420) are brought toward each other; thereby enabling the physician (PH) to more easily control and determine the configuration of end effector (500).

Figure 8B:
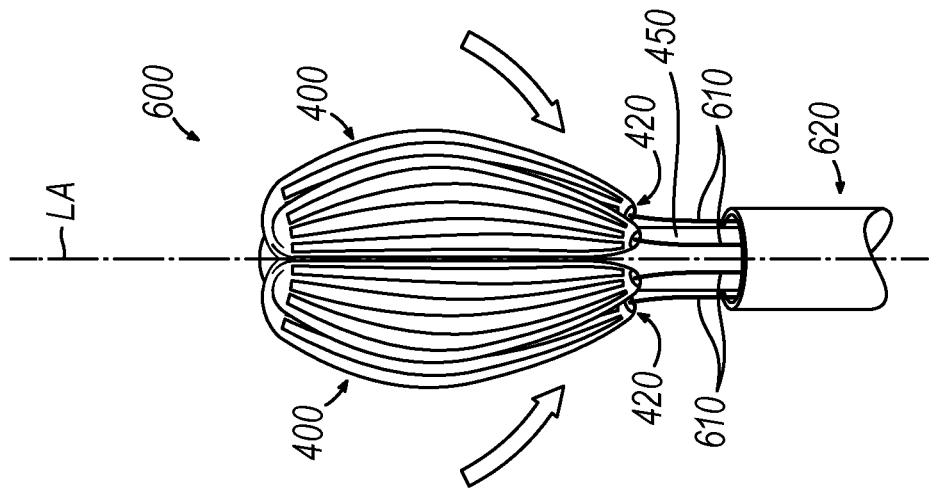
FIG. 8B depicts a side elevation view of the end effector of FIG. 8A, with the end effector in a bulbous state.
Figure 8A:
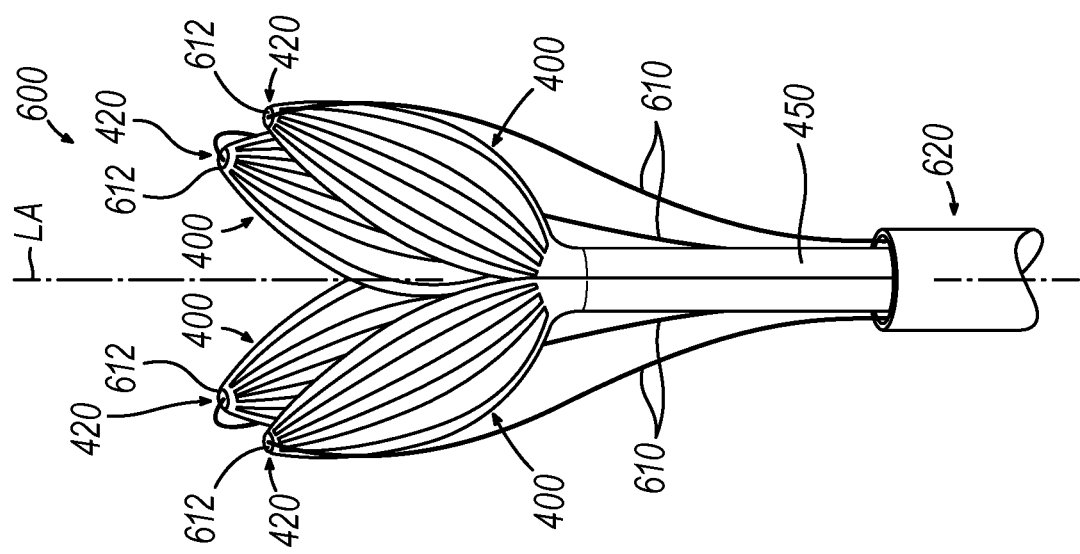
FIG. 8A depicts a side elevation view of another exemplary end effector incorporating the leaflet of FIG. 6, with the end effector in an outwardly splayed state.

FIGS. 8A-8B show another exemplary end effector (600) that includes leaflets (400) as described above. In this example, leaflets (400) retroflex in response to retraction of control wires (610) as described below. While leaflets (400) are incorporated into end effector (600) in this example, it should be understood that the below teachings may be readily applied to other versions of end effector (600) that incorporate other kinds of leaflets, including but not limited to leaflet (210) or leaflet (300). End effector (600) is at the distal end of shaft (450), which is described above as being associated with leaflets (400). At the stage shown in FIG. 8A, end effector (600) has been freed from the confines of an outer sheath (620), similar to end effector (200) being freed from the confines of the outer sheath (122) as shown in FIG. 2A. At this stage, leaflets (400) of end effector (600) are in an outwardly splayed configuration.

In the example shown in FIG. 8A, control wires (610) are secured to connection points (612) at the outer sides of distal ends (420) of leaflets (400), such that each leaflet (400) has an associated control wire (610). Control wires (610) extend along the exterior of shaft (450) and into the interior of outer sheath (620), such that leaflets (400) and shaft (450) are interposed between control wires (610) and the longitudinal axis (LA) of sheath (620). The proximal ends of control wires (610) may be coupled with a slider, a rotary knob, or any other suitable user input device at handle (110) of catheter assembly (100). When the physician (PH) wishes to transition from the outwardly splayed configuration of FIG. 8A to the bulbous configuration of FIG. 8B, the physician (PH) retracts control wires (610) proximally (e.g., by manipulating the corresponding user input device at handle (110) of catheter assembly (100)).

As control wires (610) retract proximally, distal ends (420) of leaflets (400) move through a first range of proximal motion away from the longitudinal axis (LA) of sheath (620); then through a second range of proximal motion toward the longitudinal axis (LA) of sheath (620). The proximal ends of leaflets (400) remain stationary as distal ends (420) travel through these ranges of motion. Distal ends (420) eventually reach the position shown in FIG. 8B, thereby providing end effector (600) with a bulbous configuration. In the example shown in FIGS. 8A-8B, distal ends (420) travel through a full range of motion (including the combination of the first and second ranges of proximal motion) that is greater than 90°, such that distal ends (420) are ultimately positioned longitudinally proximal to the proximal ends of leaflets (400). By contrast, in the example shown in FIGS. 7A-7B, distal ends travel through a full range of motion that is less than 90°, such that distal ends (420) are not positioned longitudinally proximal to the proximal ends of leaflets (400).

In the example of end effector (600), the resilience of leaflets (400) causes end effector (600) to have the bulbous configuration when leaflets (400) are retroflexed as shown in FIG. 8B. In other words, leaflets (400) may buckle in response to increased tension in control wires (610), thereby bowing outwardly to collectively define the bulbous shape shown in FIG. 8B. As noted above, some versions of leaflets (400) are pre-curved such that each leaflet (400) is resiliently biased to form a curved profile. In particular, each leaflet (400) may be pre-curved with a concave curvature facing toward the longitudinal axis (LA) of sheath (620) and a convex curvature facing away from the longitudinal axis (LA) of sheath (620). Such a pre-curved configuration may further promote end effector (600) defining a bulbous or spheroid shape in response to increased tension in control wires (610) as shown in FIG. 8B. As leaflets (400) travel through the ranges of motion in the transition from the state shown in FIG. 8A to the state shown in FIG. 8B, each leaflet (400) may buckle by popping outwardly, such that the concave inner side of leaflets (400) in FIG. 8A becomes a convex outer side of leaflets in FIG. 8B; and such that a convex outer side of leaflets (400) in FIG. 8A becomes a concave inner side of leaflets in FIG. 8B.

In some instances, the physician (PH) may continue retracting control wires (610) proximally after reaching the state shown in FIG. 8B. In some such cases, distal ends (420) of leaflets (400) may begin to retract further proximally, which may cause the longitudinally intermediate regions of leaflets (400) to deflect inwardly, thereby effectively narrowing the width of end effector (600) while simultaneously increasing the overall length of end effector (600). Regardless of whether the physician (PH) provides this additional narrowing of end effector (600), end effector (600) may be pressed against tissue (e.g., cardiac tissue) when end effector (600) has a bulbous shape. When end effector (600) is pressed against tissue, the leaflet (400) or leaflets (400) that is or are in contact with the tissue may deform and thereby conform to the contours of the adjacent tissue. Such deformation and conformance may promote contact between several electrodes (250, 260) of the leaflet (400) or leaflets (400) and the adjacent tissues. In some instances, such contact will effectively include a grid of electrodes (250, 260) in contact with the tissue. In the case of electrodes (250), the contact with tissue allows EP mapping of the tissue. In the case of electrodes (260), the contact with tissue allows ablation of the tissue.

When the physician (PH) wishes to return end effector (600) back to the state shown in FIG. 7A from the state shown in FIG. 7B, the physician (PH) may simply release control wires (610). With tension being relieved in control wires (610), the resilience of leaves (400) may urge end effector (600) back to the state shown in FIG. 8A. After reaching this stage, the physician may return end effector (600) to the interior of outer sheath (620) (e.g., by retracting end effector (600) proximally relative to outer sheath (620) or by advancing outer sheath (620) distally relative end effector (600)); then withdraw the catheter from the patient (PA).

While the foregoing examples describe contact between electrodes (250, 260) and tissue when end effector (500, 600) is in a bulbous shape as shown in FIGS. 7B and 8B, such contact may also be achieved when end effector (500, 600) is in a non-bulbous shape as shown in FIGS. 7A and 8A. Similar contact may be achieved when end effector (200) is in the expanded and flattened state shown in FIG. 3, with such contact being between the tissue and electrodes (250, 260) on inner surfaces (212) of leaflets (210). For instance, end effector (200) may be pressed distally against the tissue by using a stamping motion. Contact may also be achieved between tissue and electrodes (250, 260) on inner surfaces (212) of leaflets (210) or on outer surfaces (214) of leaflets when end effector (200, 500, 600) is in the state shown in FIGS. 2B, 7A, and 8A.

The method of contacting tissue, and the preferred configuration of an end effector (200, 500, 600) to provide such contact, may vary based on the particular cardiovascular region in which the tissue is located. For instance, as noted above, the bloomed or splayed configuration may be preferable for relatively fast EP mapping over a relatively flat anatomical structure (e.g., the wall of an atrium in the heart (H) or some other chamber of the heart (H): while the bulbous configuration may be preferable for relatively precise EP mapping over smaller areas (e.g., in the pulmonary vein or within smaller regions inside the heart (H)).

By way of further example only, end effector (200, 500, 600) may engage tissue in accordance with any of the various techniques shown and described in U.S. Pat. No. 9,314,299, entitled "Flower Catheter for Mapping and Ablating Veinous and Other Tubular Locations," issued Apr. 19, 2016, the disclosure of which is incorporated by reference herein in its entirety. Other suitable ways in which electrodes (250, 260) of leaflets (210, 300, 400) may be brought into contact with tissue will be apparent to those skilled in the art in view of the teachings herein.

While the foregoing examples include the use of control wires (510, 610) to transition end effector (500, 600) from the state shown in FIGS. 7A and 8A to the state shown in FIGS. 7B and 8B, various other suitable structures and techniques may be used to provide a similar transition. By way of example only, nitinol structures or other temperature sensitive structures may be configured to resiliently transition end effector (500, 600) from the state shown in FIGS. 7A and 8A to the state shown in FIGS. 7B and 8B in response to being heated to human body temperature.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a catheter shaft assembly having a proximal end and a distal end, the catheter shaft assembly defining a longitudinal axis, the catheter shaft assembly including an outer sheath with a distal end; and (b) an end effector associated with the distal end of the catheter shaft assembly, the end effector comprising a plurality of leaflets, the leaflets being configured to transition between a first configuration and a second configuration, the leaflets being configured to fit within the outer sheath in the first configuration, the leaflets being configured to expand outwardly away from the longitudinal axis in the second configuration in response to being exposed distally relative to the distal end of the outer sheath, each leaflet comprising: (i) a flexible body defining a plurality of openings, and (ii) a plurality of electrodes positioned on the flexible body.

Example 2

The apparatus of Example 1, the outer sheath being operable to translate relative to the end effector between a first longitudinal position and a second longitudinal position, the outer sheath being configured to contain the end effector in the first longitudinal position, the outer sheath being configured to expose the end effector in the second longitudinal position.

Example 3

The apparatus of Example 1, the end effector being operable to translate relative to the outer sheath between a first longitudinal position and a second longitudinal position, the end effector being configured to be contained in the outer sheath in the first longitudinal position, the end effector being configured to be exposed from the outer sheath in the second longitudinal position.

Example 4

The apparatus of any one or more of Examples 1 through 3, the leaflets being resiliently biased to expand outwardly away from the longitudinal axis in the second configuration in response to being exposed distally relative to the distal end of the outer sheath.

Example 5

The apparatus of Example 4, each leaflet including at least one resilient feature integrated into or secured to the flexible body.

Example 6

The apparatus of Example 5, the at least one resilient feature comprising nitinol.

Example 7

The apparatus of any one or more of Examples 1 through 6, each leaflet having a distal end, the leaflets being configured to diverge away from the longitudinal axis in the second configuration.

Example 8

The apparatus of any one or more of Examples 1 through 7, the body comprising an electrically insulative substrate material.

Example 9

The apparatus of Example 8, the electrically insulative substrate material being selected from the group consisting of polyimide and polyether ether ketone.

Example 10

The apparatus of any one or more of Examples 1 through 8, the body comprising a shame memory material.

Example 11

The apparatus of Example 10, the shape memory material comprising a temperature sensitive material, such that the shape memory material is configured to transition from a first shape to a second shape in response to a change in temperature.

Example 12

The apparatus of any one or more of Examples 10 through 11, the shape memory material comprising nitinol.

Example 13

The apparatus of any one or more of Examples 1 through 12, the electrodes comprising at least one pair of bipolar sensing electrodes configured to sense potentials in tissue.

Example 14

The apparatus of Example 13, the sensing electrodes including a coating configured to increase a signal-to-noise ratio of potentials picked up by the sensing electrodes.

Example 15

The apparatus of any one or more of Examples 1 through 14, the electrodes comprising at least one ablation electrode.

Example 16

The apparatus of any one or more of Examples 1 through 15, further comprising a position sensor, the position sensor being operable to generate a signal indicative of a position of one or both of at least a portion of the catheter shaft assembly or at least a portion of the end effector in three-dimensional space.

Example 17

The apparatus of Example 16, the position sensor being located on a portion of the catheter shaft assembly.

Example 18

The apparatus of Example 16, the position sensor being located in the end effector.

Example 19

The apparatus of Example 18, the position sensor being located on one of the leaflets.

Example 20

The apparatus of Example 19, further comprising a plurality of position sensors, each leaflet having at least one of the position sensors integrated into the leaflet.

Example 21

The apparatus of any one or more of Examples 1 through 20, each flexible body comprising: (A) a central spine member, and (B) a first plurality of members extending outwardly from the central spine member.

Example 22

The apparatus of Example 21, the members of the first plurality of members being straight.

Example 23

The apparatus of Example 22, the members of the first plurality of members extending obliquely relative to the central spine member.

Example 24

The apparatus of any one or more of Examples 21 through 23, each flexible body further comprising a second plurality of members, each member of the first plurality of members having a first end positioned at the central spine member, each member of the first plurality of members having a second end positioned at a member of the second plurality of members.

Example 25

The apparatus of Example 24, the members of the second plurality of members being straight.

Example 26

The apparatus of any one or more of Examples 24 through 25, the second plurality of members comprising a pair of proximal members and a pair of distal members.

Example 27

The apparatus of Example 26, the central spine member defining a central axis, the proximal members of the second plurality of members extending obliquely relative to the central axis.

Example 28

The apparatus of Example 27, the proximal members of the second plurality of members being oriented at an oblique angle relative to an axis that is perpendicular to the central axis, the oblique angle ranging from approximately 45° to approximately 60°.

Example 29

The apparatus of any one or more of Examples 21 through 28, the central spine member being straight.

Example 30

The apparatus of any one or more of Examples 1 through 29, each flexible body having a proximal end and a distal end, with a central axis passing through the proximal end and distal end of the flexible body, each flexible body further comprising a plurality of members extending from the proximal end and the distal end.

Example 31

The apparatus of Example 30, the plurality of members including proximal portions extending outwardly away from the central axis of the flexible body to diverge from the proximal end of the flexible body.

Example 32

The apparatus of any one or more of Examples 30 through 31, the plurality of members including distal portions extending toward the central axis of the flexible body to converge at the distal end of the flexible body.

Example 33

The apparatus of any one or more of Examples 30 through 32, the openings being defined between the members of the plurality of members.

Example 34

The apparatus of any one or more of Examples 30 through 33, the members of the plurality of members each including at least one straight portion.

Example 35

The apparatus of any one or more of Examples 30 through 34, the members of the plurality of members being curved such that the members bow outwardly relative to the central axis of the flexible body.

Example 36

The apparatus of any one or more of Examples 1 through 25, at least a portion of each leaflet being resiliently biased to assume a flat, planar configuration.

Example 37

The apparatus of any one or more of Examples 1 through 36, at least a portion of each leaflet being resiliently biased to assume a three-dimensionally curved configuration.

Example 38

The apparatus of any one or more of Examples 1 through 37, the leaflets being angularly spaced apart from each other equidistantly about the longitudinal axis.

Example 39

The apparatus of any one or more of Examples 1 through 38, the leaflets being further configured to transition from the second configuration to a third configuration, with distal ends of the leaflets diverging away from the longitudinal axis in the second configuration, and with distal ends of the leaflets converging toward the longitudinal axis in the third configuration.

Example 40

The apparatus of Example 39, further comprising at least one control wire operable to transition the leaflets from the second configuration to the third configuration.

Example 41

The apparatus of Example 40, the at least one control wire comprising a plurality of control wires, each control wire being secured to a distal portion of a corresponding leaflet of the plurality of leaflets.

Example 42

The apparatus of Example 41, each control wire being secured to an interior region of the corresponding leaflet of the plurality of leaflets such that the control wires are operable to draw the distal ends of the leaflets toward the longitudinal axis.

Example 43

The apparatus of Example 42, the control wires being further operable to pull the distal ends of the leaflets proximally to thereby cause the leaflets to buckle outwardly.

Example 44

The apparatus of Example 41, each control wire being secured to an exterior region of the corresponding leaflet of the plurality of leaflets such that the control wires are operable to draw the distal ends of the leaflets through a first range of motion and through a second range of motion, with the distal ends of the leaflets moving away from the longitudinal axis in the first range of motion, and with the distal ends of the leaflets moving toward the longitudinal axis in the second range of motion.

Example 45

An apparatus comprising: (a) a catheter shaft assembly having a proximal end and a distal end, the catheter shaft assembly defining a longitudinal axis, the catheter shaft assembly including an outer sheath with a distal end; and (b) an end effector associated with the distal end of the catheter shaft assembly, the end effector comprising a plurality of leaflets, each leaflet comprising: (i) a flexible body having a distal end, and (ii) a plurality of electrodes positioned on the flexible body, the end effector being operable to transition between a first configuration, a second configuration, and a third configuration, the leaflets being configured to fit within the outer sheath in the first configuration, the leaflets being configured to orient the distal ends of the flexible bodies outwardly away from the longitudinal axis in the second configuration in response to being exposed distally relative to the distal end of the outer sheath, and the leaflets being configured to orient the distal ends of the flexible bodies toward the longitudinal axis in the third configuration while being exposed distally relative to the distal end of the outer sheath.

Example 46

An apparatus comprising: (a) a catheter shaft assembly having a proximal end and a distal end, the catheter shaft assembly defining a longitudinal axis, the catheter shaft assembly including an outer sheath with a distal end; and (b) an end effector associated with the distal end of the catheter shaft assembly, the end effector comprising a plurality of leaflets, each leaflet comprising: (i) a flexible body having a distal end, and (ii) a plurality of electrodes positioned on the flexible body, the end effector being operable to transition between a first state, a second state, and a third state, the leaflets being configured to fit within the outer sheath in the first state, the leaflets being configured to present an outwardly bloomed configuration in the second state while being exposed distally relative to the distal end of the outer sheath, and the leaflets being configured to present a bulbous configuration in the third state while being exposed distally relative to the distal end of the outer sheath.

Example 47

A method comprising: (a) actuating a catheter assembly to transition an end effector from a first state to a second state, the catheter assembly including an outer sheath, the end effector comprising a plurality of leaflets, the leaflets including a plurality of electrodes, the leaflets being contained in the outer sheath in the first state, the leaflets being exposed relative to the outer sheath in the second state, distal ends of the leaflets diverging outwardly away from a longitudinal axis defined by the catheter assembly in the second state; and (b) actuating the end effector to transition from the second state to a third state, the distal ends of the leaflets converging toward the longitudinal axis in the third state.

Example 48

The method of Example 47, the step of actuating the end effector comprising retracting at least one control wire proximally to urge the distal ends of the leaflets toward the longitudinal axis.

Example 49

The method of Example 48, the retraction of the at least one control wire causing the distal ends to travel through a range of motion of at least 90°.

Example 50

The method of Example 49, the distal ends of the leaflets being positioned proximally relative to proximal ends of the leaflets in the third state.

Example 51

The method of any one or more of Examples 47 through 50, further comprising urging at least one of the electrodes against tissue.

Example 52

The method of Example 51, the tissue comprising cardiac tissue.

Example 53

The method of any one or more of Examples 51 through 52, further comprising sensing potentials in the tissue via the at least one of the electrodes.

Example 54

The method of any one or more of Examples 51 through 53, further comprising ablating the tissue via the at least one of the electrodes.

Example 55

The method of any one or more of Examples 51 through 54, further comprising tracking a position of the end effector in a patient, the tracking being provided by a position sensor.

Example 56

A catheter comprising: (a) a catheter shaft assembly having a proximal end and a distal end, the catheter shaft assembly defining a longitudinal axis, the catheter shaft assembly including an outer sheath with a distal end; and (b) an end effector associated with the distal end of the catheter shaft assembly, the end effector comprising a plurality of leaflets, each leaflet comprising: (i) a central spine extending along a center axis, (ii) a first outer member extending from a first location on the central spine to a second location on the central spine, (iii) a second outer member extending proximate the first location on the central spine to a location proximate the second location on the central spine, (iv) a plurality of connectors extending from the central spine and connected to one of the first and second outer members, and (v) a plurality of electrodes disposed on at least one of the connectors, central spine and the first and second outer members

Example 57

The catheter of Example 56, the plurality of leaflets comprising four leaflets, the leaflets being configured to transition between a first configuration and a second configuration, the leaflets being configured to fit within the outer sheath in the first configuration, the leaflets being configured to expand outwardly away from the longitudinal axis in the second configuration in response to being exposed distally relative to the distal end of the outer sheath.

VI. Miscellaneous

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

By way of example only, when one of the instruments described herein is cleaned and sterilized before and/or after a procedure such cleaning and reprocessing may be carried out using a solution. By way of further example only, such a solution may comprise a chemical selected from a group consisting of: 3300-3800 ppm peracetic acid; 2.65% glutaraldehyde; 3.4% glutaraldehyde with 26% isopropanol; 3.5% glutaraldehyde; 5.75% ortho-phthaldehyde; 0.55% ortho-phthaldehyde; hypochlorite with hypochlorous acid 650-675 ppm active free chlorine; 1.12% glutaraldehyde with 1.93% phenol/phenate; 2.5% glutaraldehyde; 3.2% glutaraldehyde; 3% glutaraldehyde; 7.35% hydrogen peroxide with 0.23% peracetic acid; 1.0% hydrogen peroxide with 0.08% peracetic acid; 2.4% glutaraldehyde; 3.4% glutaraldehyde; 2.0% hydrogen peroxide; 0.60% ortho-phthalaldehyde; hypochlorous acid/hypochlorite 400-450 ppm with active free chlorine; and combinations thereof. As another merely illustrative example, such a solution may comprise a chemical selected from a group consisting of: 3100-3400 ppm peracetic acid; 3.4% glutaraldehyde with 20.1% isopropanol; 2.0% hydrogen peroxide; at least 1820 mg/L peracetic acid; 0.575% ortho-phthalaldehyde; 0.60% ortho-phthalaldehyde; hypochlorite and hypochlorous acid with 650-675 ppm active free chlorine; 0.55% ortho-phthalaldehyde; 7.5% hydrogen peroxide; 2.6% glutaraldehyde; hypochlorite and hypochlorous acid with 400-450 ppm active free chlorine; 0.55% ortho-phthalaldehyde; and combinations thereof.

By way of example only, when one of the instruments described herein is cleaned and sterilized before and/or after a procedure such cleaning and reprocessing may be carried out using a sterilization system such as those described in U.S. Pat. No. 6,939,519, entitled "Power System for Sterilization Systems Employing Low Frequency Plasma," issued Sep. 6, 2005, the disclosure of which is incorporated by reference herein in its entirety, via the Appendix; U.S. Pat. No. 6,852,279, entitled "Sterilization with Temperature-Controlled Diffusion Path," issued Feb. 8, 2005, the disclosure of which is incorporated by reference herein in its entirety; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein in its entirety; U.S. Pat. No. 6,447,719, entitled "Power System for Sterilization Systems Employing Low Frequency Plasma," issued Sep. 10, 2002, the disclosure of which is incorporated by reference herein in its entirety; and U.S. Pub. No. 2017/0252474, entitled "Method of Sterilizing Medical Devices, Analyzing Biological Indicators, and Linking Medical Device Sterilization Equipment" published Sep. 7, 2017, issued as U.S. Pat. No. 10,561,753 on Feb. 18, 2020, the disclosure of which is incorporated by reference herein in its entirety. Some sterilization systems may use vaporized chemical sterilants or chemical gas such as hydrogen peroxide, peracetic acid, ozone, chlorine dioxide, nitrogen dioxide, etc., to sterilize medical devices. Examples of such systems are described in U.S. Pat. No. 6,365,102, entitled "Method of Enhanced Sterilization with Improved Material Compatibility," issued Apr. 2, 2002, the disclosure of which is incorporated by reference herein in its entirety; and U.S. Pat. No. 6,325,972, entitled "Apparatus and Process for Concentrating a Liquid Sterilant and Sterilizing Articles Therewith," issued Dec. 4, 2001, the disclosure of which is incorporated by reference herein in its entirety.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) a catheter shaft assembly having a proximal end and a distal end, the catheter shaft assembly defining a longitudinal axis, the catheter shaft assembly including an outer sheath with a distal end; and
    (b) an end effector associated with the distal end of the catheter shaft assembly, the end effector comprising a plurality of leaflets, the plurality of leaflets being configured to transition between a first configuration and a second configuration, the plurality of leaflets being configured to fit within the outer sheath in the first configuration, the plurality of leaflets being configured to expand outwardly away from the longitudinal axis in the second configuration in response to being exposed distally relative to the distal end of the outer sheath, the plurality of leaflets being further configured to form a bulbous shape in a third configuration, each leaflet of the plurality of leaflets comprising:
        (i) a flexible body including a planar flex circuit substrate defining a plurality of openings, and
        (ii) a plurality of electrodes positioned on the planar flex circuit substrate.

2. The apparatus of claim 1, the plurality of leaflets being resiliently biased to expand outwardly away from the longitudinal axis in the second configuration in response to being exposed distally relative to the distal end of the outer sheath.

3. The apparatus of claim 1, each leaflet of the plurality of leaflets having a distal end, the plurality of leaflets being configured to diverge away from the longitudinal axis in the second configuration.

4. The apparatus of claim 1, the plurality of electrodes comprising at least one pair of bipolar sensing electrodes configured to sense potentials in tissue.

5. The apparatus of claim 1, the plurality of electrodes comprising at least one ablation electrode.

6. The apparatus of claim 1, each flexible body comprising:
    (A) a central spine member, and
    (B) a first plurality of members extending outwardly from the central spine member.

7. The apparatus of claim 6, members of the first plurality of members being straight.

8. The apparatus of claim 7, members of the first plurality of members extending obliquely relative to the central spine member.

9. The apparatus of claim 6, each flexible body further comprising a second plurality of members, each member of the first plurality of members having a first end positioned at the central spine member, each member of the first plurality of members having a second end positioned at a member of the second plurality of members.

10. The apparatus of claim 6, the central spine member being straight.

11. The apparatus of claim 1, each flexible body having a proximal end and a distal end, with a central axis passing through the proximal end and distal end of the flexible body, each flexible body further comprising a plurality of members extending from the proximal end and the distal end.

12. The apparatus of claim 11, the plurality of members including proximal portions extending outwardly away from the central axis of the flexible body to diverge from the proximal end of the flexible body.

13. The apparatus of claim 11, the plurality of members including distal portions extending toward the central axis of the flexible body to converge at the distal end of the flexible body.

14. The apparatus of claim 1, at least a portion of each leaflet of the plurality of leaflets being resiliently biased to assume a flat, planar configuration.

15. The apparatus of claim 1, at least a portion of each leaflet of the plurality of leaflets being resiliently biased to assume a three-dimensionally curved configuration.

16. The apparatus of claim 1, the plurality of leaflets being angularly spaced apart from each other equidistantly about the longitudinal axis.

17. The apparatus of claim 1, wherein distal ends of the plurality of leaflets diverge away from the longitudinal axis in the second configuration, and wherein distal ends of the plurality of leaflets converge toward the longitudinal axis in the third configuration.

18. An apparatus comprising:
    (a) a catheter shaft assembly having a proximal end and a distal end, the catheter shaft assembly defining a longitudinal axis, the catheter shaft assembly including an outer sheath with a distal end;
(b) an end effector associated with the distal end of the catheter shaft assembly, the end effector comprising a plurality of leaflets, each leaflet of the plurality of leaflets comprising:
(i) a flexible body having a distal end, and
(ii) a plurality of electrodes positioned on the flexible body and
(c) an actuation assembly;
the end effector being operable to transition between a first configuration, a second configuration, and a third configuration,
the plurality of leaflets being configured to fit within the outer sheath in the first configuration,
the plurality of leaflets being configured to orient the distal ends of the flexible bodies outwardly away from the longitudinal axis in the second configuration in response to being exposed distally relative to the distal end of the outer sheath, and
the actuation assembly being operable to drive the distal ends of the flexible bodies proximally and toward the longitudinal axis from the second configuration to the third configuration while being exposed distally relative to the distal end of the outer sheath.

19. The apparatus of claim 18, the actuation assembly comprising a plurality of control wires, each control wire of the plurality of control wires being coupled with a corresponding leaflet of the plurality of leaflets.

20. A catheter comprising:
(a) a catheter shaft assembly having a proximal end and a distal end, the catheter shaft assembly defining a longitudinal axis, the catheter shaft assembly including an outer sheath with a distal end; and
(b) an end effector associated with the distal end of the catheter shaft assembly, the end effector comprising a plurality of leaflets, each leaflet of the plurality of leaflets comprising:
(i) a central spine coextensive with a center axis, the center axis extending outwardly from the longitudinal axis of the catheter shaft assembly,
(ii) a first outer member extending from a first location on the central spine to a second location on the central spine,
(iii) a second outer member extending proximate the first location on the central spine to a location proximate the second location on the central spine,
(iv) a plurality of connectors extending from the central spine and connected to one of the first or second outer members, and
(v) a plurality of electrodes disposed on at least one connector of the plurality connectors, the central spine, or the first and second outer members.

* * * * *